United States Patent [19]

Hayashibe et al.

[11] Patent Number: 5,178,771
[45] Date of Patent: Jan. 12, 1993

[54] METHOD FOR MEASURING IMPURITY CONCENTRATION AND REMOVING IMPURITIES FROM ELECTROLYTIC SOLUTION FOR ELECTROWINNING OF ZINC

[75] Inventors: Yutaka Hayashibe; Minoru Takeya, both of Omiya; Kazunori Yamashita; Mamoru Minami, both of Akita, all of Japan

[73] Assignee: Mitsubishi Materials Corporation, Tokyo, Japan

[21] Appl. No.: 705,324

[22] Filed: May 24, 1991

[30] Foreign Application Priority Data

May 30, 1990 [JP] Japan .................... 2-140316

[51] Int. Cl.$^5$ ............................ B01D 17/12
[52] U.S. Cl. .................... 210/709; 210/719; 210/726; 210/721; 210/745; 210/759; 423/101; 423/106; 436/55; 436/80; 436/84; 436/175; 204/114
[58] Field of Search ............ 204/55 R, DIG. 13, 55.1; 205/244; 210/709, 719, 724, 725, 726, 727, 745, 721, 759; 423/101, 106; 436/55, 80, 84, 175

[56] References Cited

U.S. PATENT DOCUMENTS

| | | | |
|---|---|---|---|
| 2,772,230 | 11/1956 | Hollander et al. | 423/101 |
| 3,898,042 | 8/1975 | Webb et al. | 436/80 |
| 3,951,602 | 4/1976 | Thompson | 436/80 |
| 4,637,832 | 1/1987 | Cammi et al. | 423/101 |

FOREIGN PATENT DOCUMENTS

| | | | |
|---|---|---|---|
| 50-17319 | 2/1975 | Japan | 204/DIG. 13 |
| 50-17335 | 2/1975 | Japan | 204/DIG. 13 |
| 557114 | 6/1977 | U.S.S.R. | 204/DIG. 13 |

Primary Examiner—Peter Hruskoci
Attorney, Agent, or Firm—Webb, Burden, Ziesenheim & Webb

[57] ABSTRACT

Concentrations of cobalt and copper of electrolysis solution for electrowinning of zinc can be measured any time during electrowinning operation by continuously sampling the solution, diluting it, adding coloring reagent to the flow of the solution and spectrophotometrically analyzing the solution.

The cobalt and copper as deleterious impurities can be removed continuously and automatically by measuring their concentrations by the above method and adding precipitation reagents for them in an amount calculated by a microcomputer on the basis of said analysis.

26 Claims, 2 Drawing Sheets

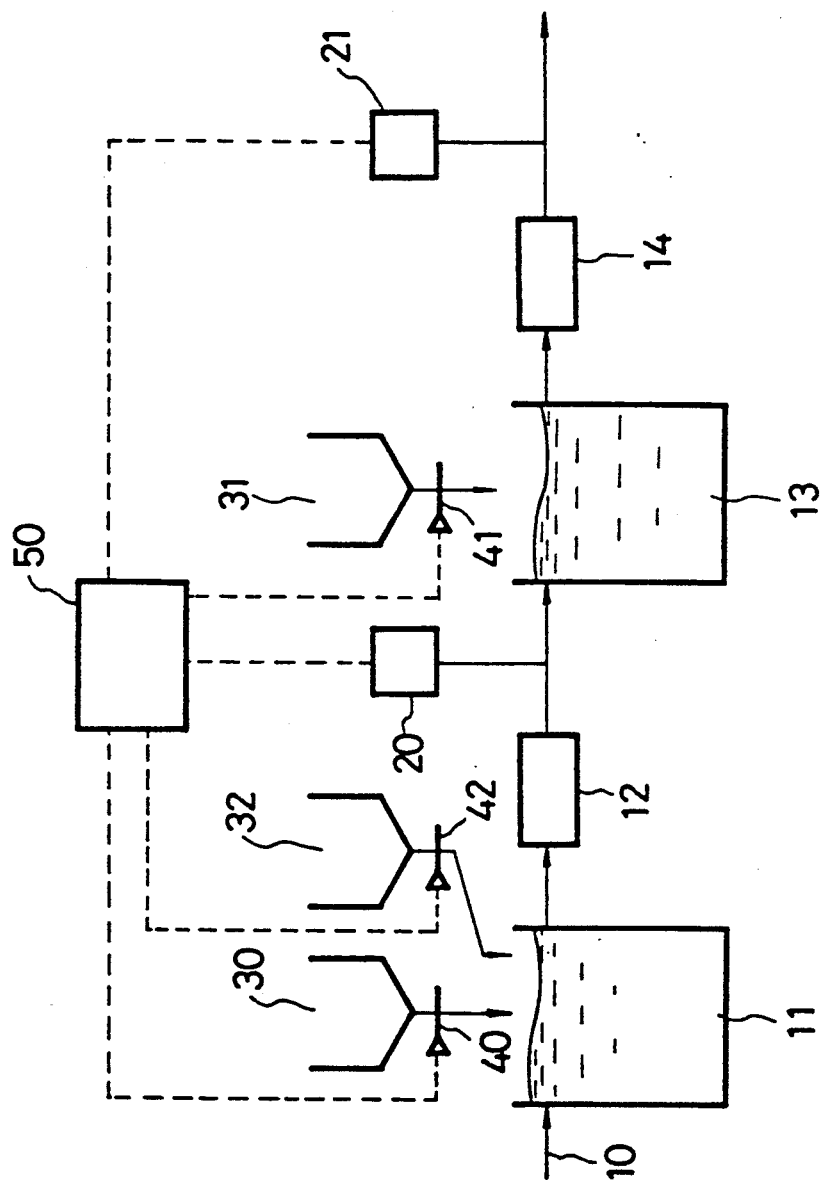

METHOD FOR MEASURING IMPURITY CONCENTRATION AND REMOVING IMPURITIES FROM ELECTROLYTIC SOLUTION FOR ELECTROWINNING OF ZINC

FIELD OF THE INVENTION

This invention relates to a method for measuring the concentrations of impurities in the electrolytic solution for electrowinning zinc and a system for automatically purifying the electrolytic solution on the basis of such measurement.

BACKGROUND OF THE INVENTION

In the electrowinning of metals having oxidation potential greater than hydrogen overvoltage, presence of impurities in the electrolytic solution causes marked impairment of electrolysis efficiency and sometimes it makes the electrolysis impossible. Therefore, usually there is provided a step for purifying the electrolysis solution wherein impurity metal ions are removed. In the case of electrowinning of zinc, the zinc sulfate electrolysis solution is purified by removing copper, cobalt, cadmium, etc. Of these, copper is precipitated by addition of zinc powder and cobalt is precipitated by addition of zinc powder and arsenic oxide ($As_2O_3$) and the precipitates are removed.

It is necessary to determine the concentrations of the impurities to be removed prior to purification. For the measurement of low concentration impurity metals, (a) colorimetric method using a coloring reagent, (b) measurement of redox potentials, (c) atomic absorption analysis, (d) Inductively coupled Plasma Atomic Emission Spectrometry (ICP) emission spectrophotometry, etc. are generally employed. In the case of zinc sulfate solution, however, manual chemical analysis is solely resorted to for the measurement of concentrations of copper and cobalt ions, since the zinc sulfate solution is a relatively viscous, acidic or weakly acidic solution with super-saturated zinc and is liable to clogging of conduits with the deposition of salts and automatic and continuous analysis is impossible. That is, samples are taken for the determination of concentration of copper and cobalt each time and the samples are subjected to classic colorimetric analysis or titration.

In the classic colorimetry, color of a sample is compared with a reference by human eye. It takes a long time and the results are not so accurate. Thus, it is an obstacle for automating the electrowinning process.

There has been an attempt to overcome this defect of the prior art. It is called "flow injection method". That is, there is provided a flow of a reagent mixture. The sample taken from the electrolysis solution is added to this flow when measurement is desired and the concentration of the object impurity is measured spectrophotometrically for instance.

This method has the following defects. 1. The sample is dispersed in a reagent solution and thus the sample is highly diluted and thus the measurement of a very slight amount of the impurity is difficult. 2. Expensive coloring reagent is wasted.

This invention is intended to overcome the abovementioned various problems and provide improved method of measurement of the impurities in the electrolysis solution for electrowinning of zinc and further to provide an automatic purifying system for electrowinning electrolysis solution for electrowinning of zinc.

SUMMARY OF THE INVENTION

This invention provides a method for measuring concentration of cobalt in the electrolytic solution for electrowinning of zinc instantly at any desired time, which comprises continuously taking out the zinc sulfate electrolytic solution from the electrolytic apparatus; continuously diluting said solution; continuously adding to the flow of the solution a buffer solution and a chelating agent for masking metal ions other than cobalt ions; adding a coloring reagent for cobalt to the thus mixed continuous flow when measurement is desired; adding a reagent for decomposing the complexes of metals other than cobalt if necessary; allowing said flow to pass through a reaction zone and finally allowing said flow to pass through a spectrophotometric means, whereby the cobalt concentration is determined.

A preferred coloring reagent for cobalt is 1-nitroso-2-naphthol-3,6-disulfate sodium (hereinafter called "nitroso R salt").

A preferred chelating reagent is a citric acid salt such as diammonium citrate (0.5M).

A preferred buffer reagent is ammonium acetate (2M).

When the above preferred reagent for decomposing the complexes of the metals other than cobalt is used, a mineral acid is used. Preferably hydrogen peroxide is used in combination with the mineral acid.

A preferred reaction zone is a spiral tube provided in a heating medium.

This invention also provides a method for measuring concentration of copper in the electrolytic solution for electrowinning of zinc instantly at any desired time, which comprises continuously taking out the zinc sulfate electrolytic solution from the electrolytic apparatus; continuously diluting said solution; continuously adding to the solution a buffer solution and a chelating agent for masking metal ions other than copper; adding a coloring reagent for copper to the thus mixed continuous flow when measurement is desired; adding a reagent for decomposing the complexes of the metals other than copper if necessary; allowing said flow to pass through a reaction zone and finally allowing said flow to pass through a spectrophotometric means, whereby the copper concentration is determined.

A preferred coloring agent for copper is bathocuproine disulfonic acid disodium, neocuproine hydrochloride, etc. Preferably an aqueous solution of ascorbic acid is used for reduction of copper ions.

When the above preferred coloring reagents are used, the reagent for decomposing the complexes is not required.

A preferred reaction zone is the same as in the case of the measurement of cobalt concentration.

This invention further provides a system for purifying the zinc sulfate electrolytic solution for electrowinning zinc, which comprises: providing a first electrolytic solution cleaning zone and a first separation zone and a second electrolytic solution cleaning zone and a second separation zone in series; continuously taking out said electrolytic solution from the electrolytic apparatus and supplying it into said first cleaning zone to let it pass through the first separation zone and the second cleaning and separation zones; continuously taking out a portion of said flowing electrolytic solution from the downstream of said first separation zone and leading it to a first analysis zone; wherein the solution is diluted, a buffer solution and a chelating solution for masking metal ions other than cobalt ions are added to said electrolytic solution, a coloring reagent for cobalt ions is added into the thus mixed continuous flow when measurement is desired and the cobalt concentration is spectrophotometrically measured; sending the analysis information to a information-processing unit wherein the amounts of zinc powder and arsenic oxide to be added to the first cleaning zone are calculated; sending the calculated information to hopper means for the first cleaning zone so as to supply the calculated amounts of zinc powder and arsenic oxide to said first cleaning zone; continuously taking out a portion of said flowing electrolytic solution from the downstream of said second separation zone and leading it to a second measurement zone; wherein a buffer solution and a chelating solution for masking metal ions other than copper ions are continuously added to said electrolytic solution, a coloring reagent for copper ions into the thus mixed continuous flow when measurement is desired and spectrophotometrically measuring the copper concentration; sending the analysis information to said information-processing unit wherein the amount of zinc powder to be added to the second cleaning zone is calculated; sending the calculated information to a hopper means for the second cleaning zone so as to supply the calculated amount of zinc powder to said second cleaning zone.

The above-mentioned preferred conditions for analysis can optionally be applied to this system.

Preferably, measurement of impurity metals is carried out periodically in accordance with the command from the information-processing unit.

If there is no necessity to separately collect cobalt and copper, purification can be carried out in one precipitation tank.

BRIEF DESCRIPTION OF THE DRAWINGS

FIG. 2 is a schematic representation of the system and apparatus for purifying the electrolysis solution in accordance with the present invention.

DESCRIPTION OF SPECIFIC EMBODIMENT OF THE INVENTION

Figure 1:
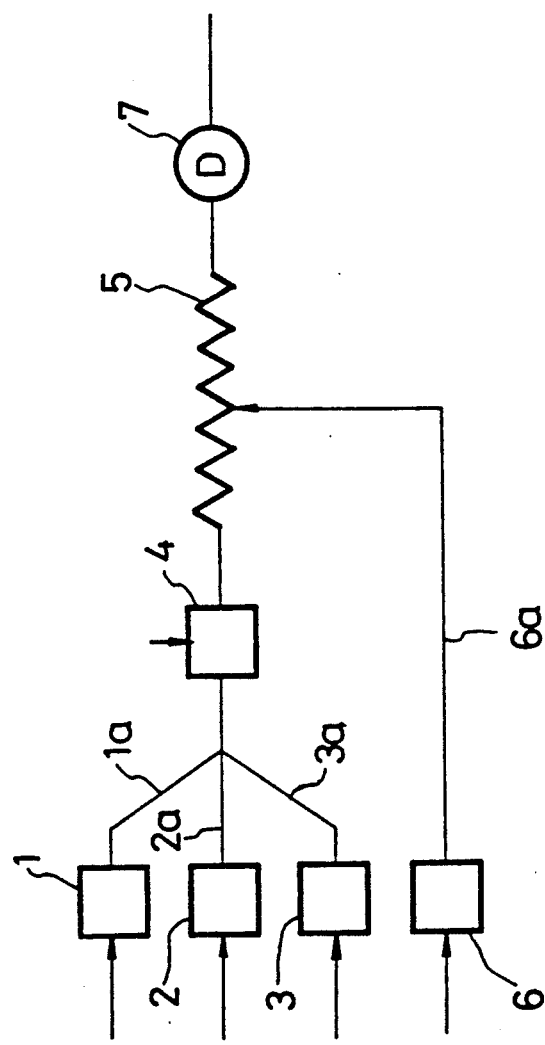
FIG. 1 is a schematic representation of the method and apparatus for measurement of impurity concentration in accordance with the present invention.

Now the invention will be specifically described with reference to the attached drawings.

FIG. 1 shows the method and apparatus of the analysis in accordance with the present invention.

The apparatus for the analysis substantially comprises a long tube system having an inside diameter of 1 mm with several instruments incorporated therein.

Zinc sulfate electrolysis solution is continuously taken from the electrolysis bath by means of a pump 1 and a conduit 1a. Water (containing 0.25M $H_2SO_4$) for dilution is continuously added to the solution through a pump 2 and a conduit 2a and a reagent solution containing a buffer reagent and a chelating reagent is added to the electrolysis solution by means of a pump 3 and a conduit 3a. These can be plunger pumps. To this flow of the mixed solution, a coloring reagent for the object metal is added to the solution at the station 4. The thus mixed solution is passed through a reaction zone 5, at least a part of which can be heated. In the reaction zone which is a part of a measurement zone, another reagent can be added by means of a pump 6 and a conduit 6a. The solution which has passed the reaction zone is passed through a spectrophotometric means 7, wherein the concentration of the object metal is spectrophotometrically determined.

The apparatus represented by FIG. 1 is indicated as an analysis zone as a whole in FIG. 2.

FIG. 2 shows for the electrolysis-solution-purifying system of the present invention.

Zinc sulfate electrolysis solution is taken from the electrolysis bath through a conduit 10 and transferred to a first purifying zone (tank) 11, wherein the solution is stirred by a stirrer not shown. The solution is overflown to a second purifying zone (tank) 13 through a first separator 12 which may be a filter. Arsenic oxide and zinc powder are continuously fed into the purifying tanks 11 and 12 respectively. A portion of the solution is taken from the conduit after the first separator 12 and sent to a first analysis zone 20, wherein the cobalt concentration is spectrophotometrically determined. The result of the analysis is sent to an information processing unit 50, wherein the amounts of zinc powder and arsenic oxide to be added to the first purifying tank are calculated and the resulting information is sent to valve means 40 and 42 of an zinc powder hopper 30 and an arsenic oxide hopper 32 so that necessary amounts of zinc powder and arsenic oxide are added to the first purifying tank 11.

From the conduit after the second separator 14, a portion of the solution is taken and sent to a second analysis zone 21, wherein the copper concentration is spectrophotometrically determined. The result is sent to the information processing unit 50 and the amount of zinc powder to be added to the second purifying tank 13 is calculated. The resulting information is sent to a valve 41 of a zinc powder hopper 31 so that a necessary amount of zinc powder is added to the second purifying tank.

Preferably, analysis is carried out periodically in accordance with the command from the information-processing unit.

Further the invention will be illustrated by way of working examples. Basic Experiment Standard solutions of zinc sulfate and nitroso R salt were prepared. Zinc sulfate solutions of various concentrations were colorimetrically measured with nitroso R salt and the results were compared the results with respect to the actual electrolysis solution for electrowinning of zinc. It was established that the measurement curve for standard solutions well corresponds to the curve for actual electrolysis solution.

Separately, the cobalt concentration of the actual electrolysis solution was measured by atomic absorption analysis and the results were compared with the results of the present method. Examples of such comparison are as follows:

| Samples | Present Invention | Atomic Absorption |
| --- | --- | --- |
| A | 0.12 ppm | 0.11 ppm |
| B | 0.068 ppm | 0.070 ppm |

It is understood that the present method is practically useful.

EXAMPLE 1

Measurement of Cobalt Concentration

Using an apparatus represented by FIG. 1, concentration of cobalt in an electrolysis solution for zinc electrowinning was measured.

An electrolysis solution was taken from the electrolytic bath at a rate of 0.3 ml per min. and diluted to 5 times. To the flow of the diluted solution, a 2M ammonium acetate-0.5M diammonium citrate solution was continuously added at a rate of 1.5 ml per min. And 60 $\mu$l of a 1% solution of nitroso R salt was added by means of a syringe pump (a syringe with a stop valve). The thus mixed solution was passed through the reaction zone heated to 80° C. during which 2M nitric acid solution containing 0.5% hydrogen peroxide solution at a rate of 2 ml per min. in order to decompose complexes of metals other than cobalt.

The solution is led to a spectrophotometer, Ratiobeam U-1000 manufactured by Hitachi, Ltd., wherein light absorption at 520 nm was measured. The electrolysis solution contained 0.12 ppm of cobalt.

EXAMPLE 2

Measurement of Copper Concentration

Using the same apparatus, copper concentration of the same electrolysis solution was measured.

The electrolysis solution was taken from the electrolytic bath at a rate of 0.3 ml per min. and diluted to 5 times. To the flow of the diluted solution, a 2M ammonium acetate-0.5M diammonium citrate solution was continuously added at a rate of 1.5 ml per min. Further a 0.05% solution of bathocuproine disulfonic acid disodium was added. The thus mixed solution was passed through the reaction zone at room temperature.

The solution is led to a spectrophotometer, Ratiobeam U-1000 manufactured by Hitachi, Ltd., wherein light absorption at 525 nm was measured. The electrolysis solution contained 0.5 ppm of copper.

EXAMPLE 3

Purification of Electrolysis Solution

The same electrolysis solution was purified in accordance with the system of the present invention using an apparatus represented by FIG. 2.

The approximate capacity of the cleaning tanks 11 and 13 was 150 m$^3$.

The analysis sections 20 and 21 were the same as described above with respect to the measurement of concentrations of cobalt and copper.

The separators 12 and 14 were filter presses.

The valve 40, 41 and 42 were screw feeders.

The information processing unit used was a "NEC PC9801" personal computer.

The electrolysis solution was drawn into the first cleaning tank 11 at a rate of 200 l/min and the residence time in the tank 11 was about 40 min.

The hopper 30 contained arsenic oxide and the hopper 31 and 32 contained zinc powder.

Analysis was carried out every 10 minutes in accordance with the command from the information-processing unit 50. Thus the amounts of arsenic and zinc powder to be added were well regulated, nearly continuously.

Prior to the present invention, the measurement of the impurity metals was carried out only every one hour because of the time-consuming manual analysis. Thus the regulation of the amounts of zinc powder and arsenic oxide was manually conducted intermittently only once in an hour. Therefore, purification could not be follow the fluctuation of the impurity concentration and there were overs and shorts in supplying the precipitation reagents.

We claim:

1. A method for measuring the concentration of cobalt in a zinc sulfate electrolytic solution in an electrolytic apparatus for electrowinning of zinc, instantly at any desired time, which comprises continuously taking out the zinc sulfate electrolytic solution from the electrolytic apparatus; continuously diluting said solution; continuously adding to the flow of the solution a buffer solution and a chelating agent, said chelating agent forming complexes of metals for masking metal ions other than cobalt ions; adding a coloring reagent for cobalt to the thus mixed continuous flow during said measuring; optionally adding a reagent for decomposing the complexes of metals other than cobalt; allowing said flow to pass through a reaction zone and finally allowing said flow to pass through a spectrophotometric means, wherein the cobalt concentration is determined.

2. A method as claimed in claim 1, wherein the coloring reagent is 1-nitroso-2-naphthol-3,6-disulfate sodium.

3. A method as claimed in claim 1, wherein the chelating agent is a citric acid salt.

4. A method as claimed in claim 1, wherein the buffer reagent is ammonium acetate.

5. A method as claimed in claim 1, wherein the reagent for decomposing the complexes other than cobalt is a mineral acid.

6. A method as claimed in claim 5, further comprising the step of adding the mineral acid in a solution containing hydrogen peroxide.

7. A method as claimed in claim 1, wherein the reaction zone is a spiral tube provided in a heating medium.

8. A method for measuring the concentration of copper in a zinc sulfate electrolytic solution in an electrolytic apparatus for electrowinning of zinc instantly at any desired time, which comprises continuously taking out the zinc sulfate electrolytic solution from the electrolytic apparatus; continuously diluting said solution; continuously adding to the solution a buffer solution and a chelating agent, said chelating agent forming complexes of metals for masking metal ions other than copper ions; adding a coloring reagent for copper to the thus mixed continuous flow during said measuring; optionally adding a reagent for decomposing the complexes of metals other than copper; allowing said flow to pass through a reaction zone and finally allowing said flow to pass through a spectrophotometric means, whereby the copper concentration is determined.

9. A method as claimed in claim 8, wherein said coloring reagent for copper is selected from the group comprising bathocupproine disulfonic acid disodium and neocuproine hydrochloride.

10. A method as claimed in claim 8, wherein the chelating agent is a citric acid salt.

11. A method as claimed in claim 8, wherein the buffer agent is ammonium acetate.

12. A method as claimed in claim 8, wherein the reaction zone is a spiral tube provided in a heating medium.

13. A method as claimed in claim 8, further comprising the step of adding an aqueous solution of ascorbic acid to reduce said copper.

14. A method as claimed in claim 8, wherein the reagent for decomposing the complexes other than copper is a mineral acid.

15. A method as claimed in claim 14, further comprising the step of adding the mineral acid in a solution containing hydrogen peroxide.

16. A method for purifying a zinc sulfate electrolytic solution in an electrolytic apparatus for electrowinning zinc, which comprises:

providing a first electrolytic solution cleaning zone and a first separation zone and a second electrolytic solution cleaning zone and a second separation zone in series; continuously taking out said electrolytic solution from the electrolytic apparatus and supplying said solution into said first cleaning zone to let said solution pass through the first separation zone and the second cleaning and separation zones; continuously taking out a portion of said flowing electrolytic solution from the downstream of said first separation zone and leading said portion of said solution to a first analysis zone for measuring the cobalt concentration in said solution; wherein the portion of said solution is diluted, a buffer solution and a chelating agent, said chelating agent forming complexes of metals for masking metal ions other than cobalt ions are added to said electrolytic solution, a coloring reagent for cobalt ions is added into the thus mixed continuous flow during said measuring and optionally a reagent for decomposing the complexes of metals other than cobalt is added and spectrophotometrically measuring the cobalt concentration to provide a first analysis information; sending the first analysis information to an information-processing unit wherein amounts of zinc powder and arsenic oxide to be added to the first cleaning zone to precipitate said cobalt are calculated as a first calculated information based upon said first analysis information; sending the first calculated information to a means for the first cleaning zone so as to supply a calculated amount of zinc powder and arsenic oxide to said first cleaning zone wherein the precipitated cobalt is removed in said first separating zone; continuously taking out a portion of said flowing electrolytic solution from the downstream of said second separation zone and leading said portion of said solution to a second analysis zone for measuring the copper concentration in said solution; wherein a buffer solution and a chelating agent, said chelating agent forming complexes of meals for masking metal ions other than copper ions are continuously added to said portion of said electrolytic solution, a coloring reagent for copper ions is added into the thus mixed continuous flow during said measuring and optionally a reagent for decomposing the complexes of metals other than copper is added and spectrophotometrically measuring the copper concentration to provide a second analysis information; sending the second analysis information to said information-processing unit wherein an amount of zinc powder to be added to the second cleaning zone is calculated as a second calculated information based upon said second analysis information; sending the second calculated information to a means for the second cleaning zone so as to supply a calculated amount of zinc powder to said second cleaning zone to precipitate said copper wherein the precipitated copper is removed in said second separating zone.

17. A method as claimed in claim 16, wherein the analysis is periodically carried out in accordance with commands from the information-processing unit.

18. A method as claimed in claim 16, wherein the precipitation of cobalt and the precipitation of copper are carried out in one purifying zone.

19. A method as claimed in claim 16, wherein the buffer reagent is ammonium acetate.

20. A method as claimed in claim 16, wherein the chelating agent is a citric acid salt.

21. A method as claimed in claim 16, wherein the coloring reagent for cobalt is 1-nitroso-2-naphthol-3,6-disulfate sodium.

22. A method as claimed in claim 16, wherein said coloring agent for copper is selected rom the group comprising bathocupproine disulfonic acid disodium and neocuproine hydrochloride.

23. A method as claimed in claim 16, wherein the reagent for decomposing the complexes other than cobalt is a mineral acid.

24. A method as claimed in claim 23, further comprising the step of adding the mineral acid in a solution containing hydrogen peroxide.

25. A method as claimed in claim 16, wherein the reagent for decomposing the complexes other than copper is a mineral acid.

26. A method as claimed in claim 25, further comprising the step of adding the mineral acid in a solution containing hydrogen peroxide.

* * * * *

UNITED STATES PATENT AND TRADEMARK OFFICE
CERTIFICATE OF CORRECTION

PATENT NO. : 5,178,771

DATED : January 12, 1993

INVENTOR(S) : Yutaka Hayashibe, Minoru Takeya, Kazunori Yamashita and Mamoru Minami It is certified that error appears in the above-identified patent and that said Letters Patent is hereby corrected as shown below:

Column 1 Line 34 "coupled" should read --Coupled--.

Column 3 Line 6 "a" should read --an--.

Column 4 Line 25 "an zinc" should read --a zinc--.

Column 4 Line 50 after "compared" insert --with--.

Column 6 Lines 3-4 after "not" delete --be--.

Claim 16 Line 2 Column 8 "meals" should read --metals--.

Claim 22 Line 36 Column 8 "rom" should read --from--.

Signed and Sealed this

Ninth Day of November, 1993

*Attest:*

BRUCE LEHMAN

*Attesting Officer*     *Commissioner of Patents and Trademarks*